(12) United States Patent
Zhang (10) Patent No.: US 10,433,772 B2
(45) Date of Patent: Oct. 8, 2019

(54) FINGERPRINT SENSOR AND TERMINAL USING THE SAME

(71) Applicant: Guangdong Oppo Mobile Telecommunications Corp., Ltd., Dongguan, Guangdong (CN)

(72) Inventor: Wenzhen Zhang, Guangdong (CN)

(73) Assignee: Guangdong Oppo Mobile Telecommunications Corp., Ltd., Dongguan (CN)

( * ) Notice: Subject to any disclaimer, the term of this patent is extended or adjusted under 35 U.S.C. 154(b) by 134 days.

(21) Appl. No.: 15/668,006

(22) Filed: Aug. 3, 2017

(65) Prior Publication Data
US 2018/0049674 A1    Feb. 22, 2018

(30) Foreign Application Priority Data

Aug. 16, 2016  (CN) .......................... 2016 1 0677148
Aug. 16, 2016  (CN) ..................... 2016 2 0891207 U (51) Int. Cl.
| | |
|---|---|
| *A61B 5/117* | (2016.01) |
| *G01B 7/28* | (2006.01) |
| *G06K 19/08* | (2006.01) |
| *G01B 11/24* | (2006.01) |
| *H01L 27/146* | (2006.01) |

(Continued)

(52) U.S. Cl.
CPC ................ *A61B 5/117* (2013.01); *G01B 7/28* (2013.01); *G01B 11/24* (2013.01); *G06K 19/08* (2013.01); *H01L 27/146* (2013.01); *H04M 1/026* (2013.01); *A61B 5/00* (2013.01); *G06F 1/1684* (2013.01); *G06K 9/00* (2013.01); *H04M 2250/12* (2013.01)

(58) Field of Classification Search
CPC .. A61B 5/00; A61B 5/117; G01B 7/28; G01B 11/24; H04M 2250/12; G06K 19/08
See application file for complete search history.

(56) References Cited

U.S. PATENT DOCUMENTS 9,524,413 B2 * 12/2016 Kim ..................... G06K 9/0002
10,007,343 B2 * 6/2018 Kim ........................ G06F 3/016
(Continued)

FOREIGN PATENT DOCUMENTS

| CN | 101131945 A | 2/2008 |
|---|---|---|
| CN | 100483659 C | 4/2009 |

(Continued)

OTHER PUBLICATIONS

Extended European Search Report issued in corresponding European Application No. 17183110.0 dated Jan. 29, 2018 (8 pp).
(Continued)

*Primary Examiner* — Utpal D Shah
(74) *Attorney, Agent, or Firm* — Young Basile Hanlon & MacFarlane, P.C.

(57) ABSTRACT

A fingerprint sensor and a related terminal are provided. The fingerprint sensor includes a chip assembly and a protection element. The chip assembly includes a circuit board and a sealing element laminated on the circuit board. The protection assembly includes a first protection element. The circuit board is engaged with the first protection element to define a space to receive the sealing element, or the sealing element is engaged with the first protection element to define a space to receive the circuit board.

15 Claims, 9 Drawing Sheets

(51) Int. Cl.
*H04M 1/02* (2006.01)
*A61B 5/00* (2006.01)
*G06K 9/00* (2006.01)
*G06F 1/16* (2006.01)

(56) References Cited

U.S. PATENT DOCUMENTS

| | | | | |
|---|---|---|---|---|
| 10,089,517 | B2* | 10/2018 | Hsu | G06K 9/00053 |
| 10,128,907 | B2* | 11/2018 | He | H04B 5/0012 |
| 10,141,237 | B2* | 11/2018 | Lu | H01L 23/3142 |
| 10,146,982 | B2* | 12/2018 | Hsu | G06K 9/00013 |
| 2010/0039121 | A1 | 2/2010 | Iliev et al. | |
| 2011/0309482 | A1 | 12/2011 | Salatino et al. | |
| 2014/0205161 | A1* | 7/2014 | Salatino | G06K 9/00053 |
| | | | | 382/124 |
| 2015/0071509 | A1* | 3/2015 | Myers | G06K 9/0002 |
| | | | | 382/124 |
| 2016/0131505 | A1* | 5/2016 | Rao | G06K 9/0002 |
| | | | | 73/431 |
| 2016/0335468 | A1* | 11/2016 | Long | G06K 9/0002 |

FOREIGN PATENT DOCUMENTS

| | | |
|---|---|---|
| CN | 205318405 U | 6/2016 |
| CN | 105825165 A | 8/2016 |
| CN | 105844219 A | 8/2016 |
| CN | 206178868 U | 5/2017 |
| DE | 102013005500 A1 | 10/2013 |
| WO | 2016036046 A1 | 3/2016 |

OTHER PUBLICATIONS

International Search Report issued in corresponding International Application No. PCT/CN2017/094977 dated Nov. 16, 2017 (12 pp).

* cited by examiner

FINGERPRINT SENSOR AND TERMINAL USING THE SAME

CROSS-REFERENCE TO RELATED APPLICATION(S)

This application claims priority to Chinese Patent Application No. 201620891207.7, filed on Aug. 16, 2016, and Chinese Patent Application No. 201610677148.8, filed on Aug. 16, 2016, the content of both of which are hereby incorporated by reference in their entireties.

TECHNICAL FIELD

The present disclosure relates to terminals, and particularly to a fingerprint sensor and a terminal using the same.

BACKGROUND

A fingerprint sensor may generally include a chip assembly and a protection assembly. The protection assembly can protect the chip assembly, and increase the rigidity of the chip assembly, so that it is convenient to mount the fingerprint sensor in the terminal. The chip assembly may include an outer surface and an inner surface. The outer surface is exposed outside of the terminal, so that the outer surface can be touched. The protection element generally covers the outer surface or the inner surface, which may increase the thickness of the fingerprint sensor, so that the fingerprint sensor may not be suitable for a thin terminal.

BRIEF DESCRIPTION OF THE DRAWINGS

In order to illustrate the technical solutions of the implementations of the present disclosure more clearly, the drawings used in the description of the implementations will be briefly described, it will be apparent that the drawings described in the following are implementations of the present disclosure, and it will be apparent to those skilled in the art that other drawings can be obtained from the drawings without any creative work.

DETAILED DESCRIPTION

Implementations of the present disclosure will be described in detail in the following descriptions, examples of which are shown in the accompanying drawings, in which the same or similar elements and elements having same or similar functions are denoted by like reference numerals throughout the descriptions. The implementations described herein with reference to the accompanying drawings are explanatory and illustrative, which are just used to illustrate the present disclosure, and shall not be construed to limit the present disclosure.

In the description of the present disclosure, it is to be understood that orientations or position relationships illustrated by terms such as "central," "longitudinal," "lateral," "length," "width," "thickness," "upper," "lower," "front," "rear," "left," "right," "vertical," "horizontal," "top," "bottom," "inner," "outer," "clockwise," and "counterclockwise" are based on orientation or position relationship based on the accompanying drawings, and are not used to indicate or imply the devices or elements must have specific orientations, and must be constructed and operated in specific orientations, and shall not be construed to limit the present disclosure. In addition, terms such as "first" and "second" are used herein for purposes of description and are not intended to indicate or imply relative importance or significance or to imply the number of indicated technical features. Thus, the feature defined with "first" and "second" may include one or more of this feature. In the description of the present disclosure, "a plurality of" or "a number of" means two or more than two, unless specified otherwise.

In the present disclosure, unless specified or limited otherwise, the terms "mounted," "connected," "coupled," and the like are used broadly, and may be, for example, fixed connections, detachable connections, or integral connections; may also be mechanical or electrical connections; may also be direct connections or indirect connections via intervening structures; may also be inner communications of two elements or mutual interaction relationship between two elements. Those skilled in the art can understand specific meaning of the above terms in the present disclosure according to specific situations.

In the present disclosure, unless specified and limited otherwise, a first feature "on" or "below" a second feature may include that the first feature is in direct contact with the second feature, and may also include that the first feature and the second feature are not in direct contact with each other, but are contacted via an additional feature formed therebetween. Furthermore, the first feature "on," "above," or "on top of" a second feature may include that the first feature is right or obliquely "on," "above," or "on top of" the second feature, or just means that the first feature is at a height higher than that of the second feature. The first feature "below," "under," or "on bottom of" the second feature may include that the first feature is right or obliquely "below,"

"under," or "on bottom of"the second feature, or just means that the first feature is at a height lower than that of the second feature.

Various implementations and examples are provided in the following description to implement different structures of the present disclosure. In order to simplify the present disclosure, elements and settings of specific examples will be described. Certainly, these elements and settings are only examples and are not intended to limit the present disclosure. In addition, reference numerals may be repeated in different examples of the present disclosure. This repeating is for the purpose of simplification and clarity and does not refer to relations between different implementations and/or settings. Furthermore, examples of different processes and materials are provided in the present disclosure. However, it would be appreciated by those skilled in the art that other processes and/or materials may be also applied.

The following will further illustrate implementations of the present disclosure in detail in combination with the accompanying drawings.

Terminals illustrate in implementations of the present disclosure may be mobile terminals or fixed terminals. The mobile terminals may be mobile phones, tablet computers, onboard computers, and so on. The fixed terminals may be desktop computers, automatic teller machines, and so on.

Figure 1:
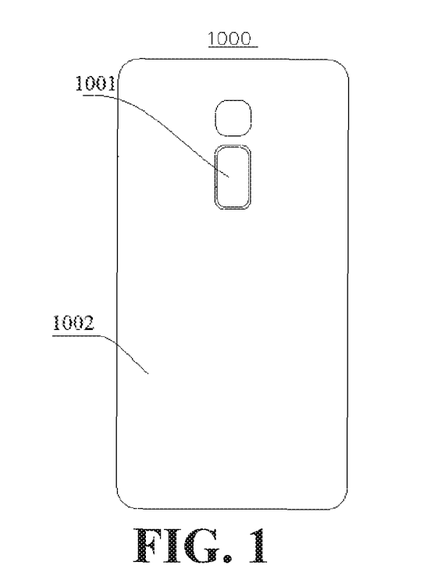
FIG. 1 is a structural view of a terminal in accordance with an implementation of the present disclosure, illustrating that a fingerprint sensor is exposed outside of a rear cover of the fingerprint sensor.

FIG. 1 is a structural view of a terminal in accordance with an implementation of the present disclosure. A terminal 1000 may include a fingerprint sensor 1001. The fingerprint sensor 1001 is exposed outside of a rear cover 1002 of the terminal 1000. The rear cover 1002 may define a through hole (not indicated) to expose the fingerprint sensor 1001 outside of the rear cover 1002. A user can touch the fingerprint sensor 1001 to input an instruction, for example, an unlock instruction, an image photographing instruction, or the like. When the fingerprint sensor 1001 is exposed outside of the rear cover 1002 of the terminal 1000, the fingerprint sensor 1001 is generally arranged to be adjacent to a rear camera of the terminal 1000, so that it is convenient to touch the fingerprint sensor 1001. The fingerprint sensor 1001 may also be arranged at other positions, and the present disclosure is not limited thereto.

Figure 2:
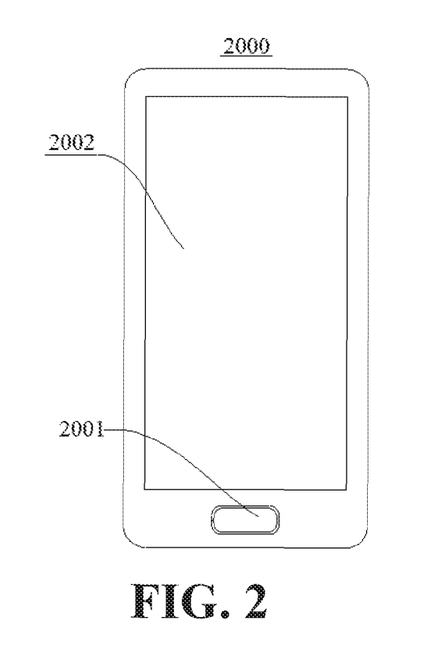
FIG. 2 is a structural view of a terminal in accordance with another implementation of the present disclosure, illustrating that the fingerprint sensor is exposed outside of a front surface of the terminal.

FIG. 2 is a structural view of a terminal in accordance with another implementation of the present disclosure. A terminal 2000 may include a fingerprint sensor 2001. The fingerprint sensor 2001 is exposed outside of a front surface of the terminal 2000 where a display screen 2002 is located, that is, the fingerprint sensor 2001 is arranged on a position of a peripheral side surrounding the display screen 2002. When the fingerprint sensor 2001 is exposed outside of the front surface of the terminal 2000, the fingerprint sensor 2001 is generally located below the display screen 2002, so that it is convenient to touch the fingerprint sensor 2001. The fingerprint sensor 2001 may also be arranged at other positions, and the present disclosure is not limited thereto.

What is needed to be illustrated is that the fingerprint sensor 1001 may be a fingerprint sensor 100 or a fingerprint sensor 200 illustrated in the following descriptions, and the fingerprint sensor 2001 may be also the fingerprint sensor 100 or the fingerprint sensor 200 illustrated in the following descriptions.

Figure 3:
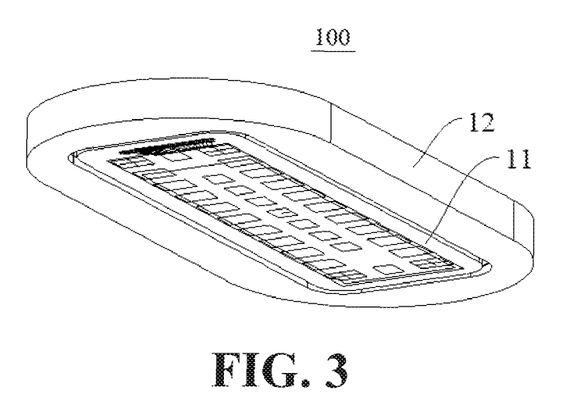
FIG. 3 is a perspective view of a fingerprint sensor in accordance with an implementation of the present disclosure.

FIG. 3 is a perspective view of a fingerprint sensor in accordance with an implementation of the present disclosure. The fingerprint sensor 100 may include a chip assembly 11 and a protection assembly 12. The protection assembly 12 may surround a peripheral side of the chip assembly 11 to protect the chip assembly 11 and increase the rigidity of the fingerprint sensor 100, so that it is convenient to mount the fingerprint sensor 100. In the implementation, the protection assembly 12 surrounds the whole peripheral side of the chip assembly 11. Certainly, it can be understood that in other implementations the protection assembly 12 may surround a portion of the peripheral side of the chip assembly 11, for example, a half of the peripheral side of the chip assembly 11.

Figure 4:
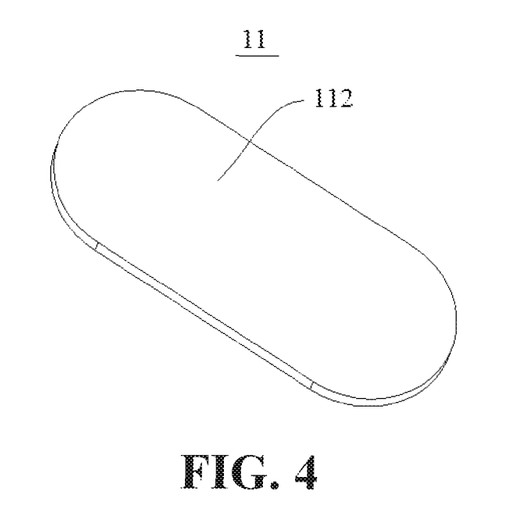
FIG. 4 is a perspective view of a chip assembly of the fingerprint sensor of FIG. 3.
Figure 5:
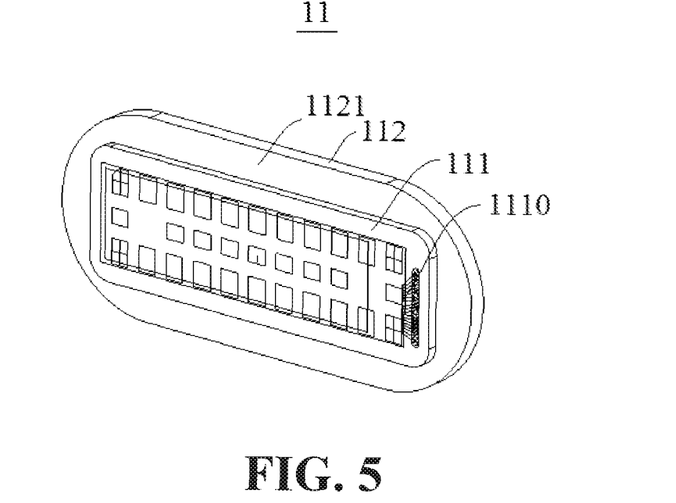
FIG. 5 is a perspective view of the chip assembly of the fingerprint sensor of FIG. 3, viewed from another viewpoint.
Figure 6:
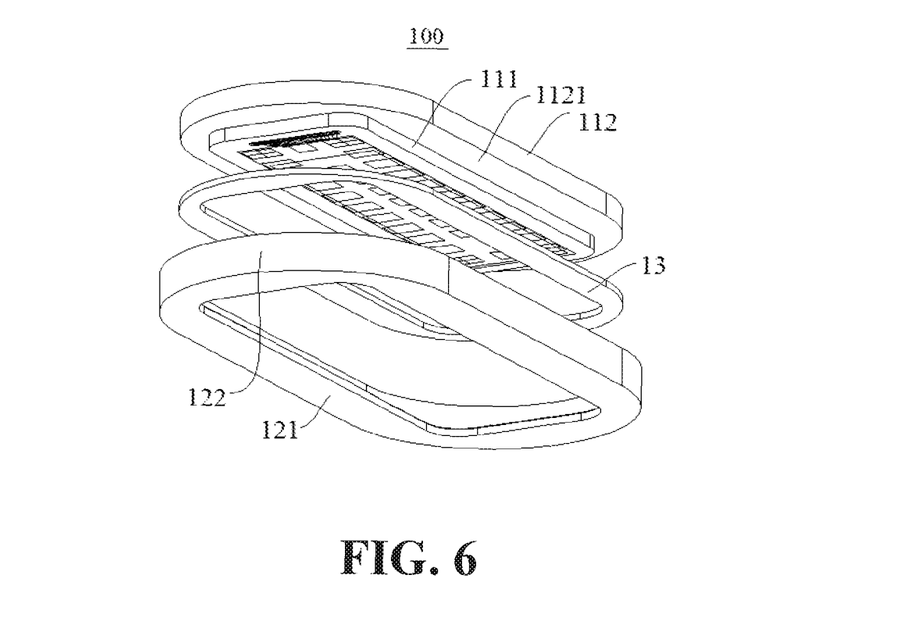
FIG. 6 is an exploded view of the fingerprint sensor of FIG. 3.

Referring to FIGS. 4-6, the chip assembly 11 may include a circuit board 111 and a sealing element 112 laminated on the circuit board 111. The sealing element 112 may be made from epoxy molding compound (EMC). The circuit board 111 protrudes from the sealing element 112. The sealing element 112 may include a limitation surface 1121 surrounding the circuit board 111. In the implementation, the limitation surface 1121 is annular. Certainly, in other implementations, the limitation surface 1121 may be other shapes, and the present disclosure is not limited thereto.

The protection assembly 12 may include a first protection element 121 and a second protection element 122. The first protection element 121 is engaged with the limitation surface 1121 to surround the circuit board 111. In the implementation, the first protection element 121 is annular. Certainly, in other implementations, the first protection element 121 may be other shapes, what is needed is that the first protection element 121 can be engaged with the limitation surface 1121. The second protection element 122 protrudes from a side of the first protection element 121 away from the circuit board 111 and surrounds the whole peripheral side of the sealing element 112 or a portion of the peripheral side of the sealing element 112.

In the implementation, the first protection element 121 is fixed to the limitation surface 1121 via an adhesive layer 13, so that the protection assembly 12 can be fixed to the chip assembly 11. Certainly, in other implementations, the second protection element 122 may be fixed to the peripheral side of the sealing element 112, so that the protection assembly 12 can also be fixed to the chip assembly 11. Furthermore, the thickness of the first protection element 121 may be substantially the same as or less than that of the circuit board 111, or a sum of the thickness of the first protection element 121 and the thickness of the adhesive layer 13 may be substantially the same as or less than that of the circuit board 111, so that the first protection element 121 is not higher than the circuit board 111.

In the implementation, the first protection element 121 is engaged with the limitation surface 1121 of the sealing element 112 surrounding the circuit board 111. Thus, the fingerprint sensor 100 is not thick due to the protection assembly 12, so that the fingerprint sensor 100 is suitable for a thin terminal.

Figure 7:
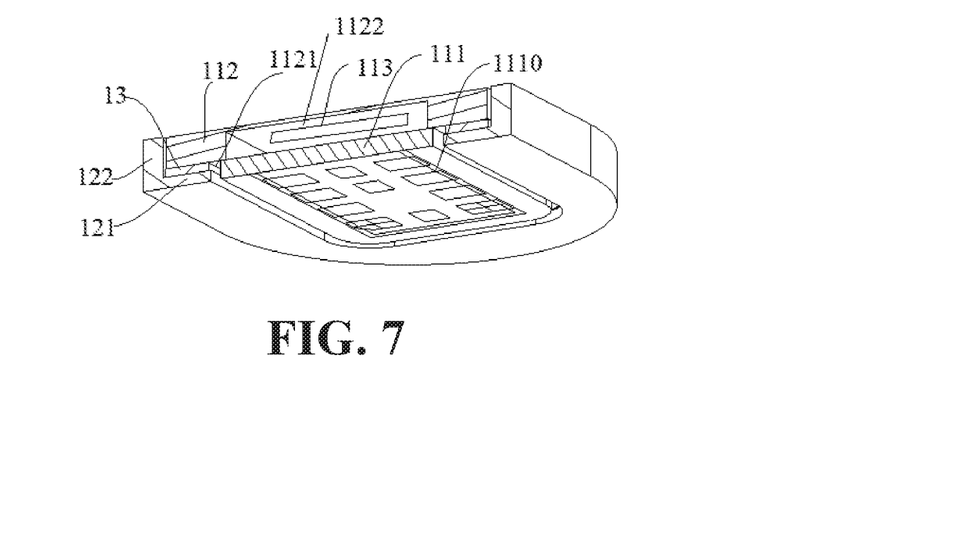
FIG. 7 is a sectional view of the fingerprint sensor of FIG. 3.
Figure 8:
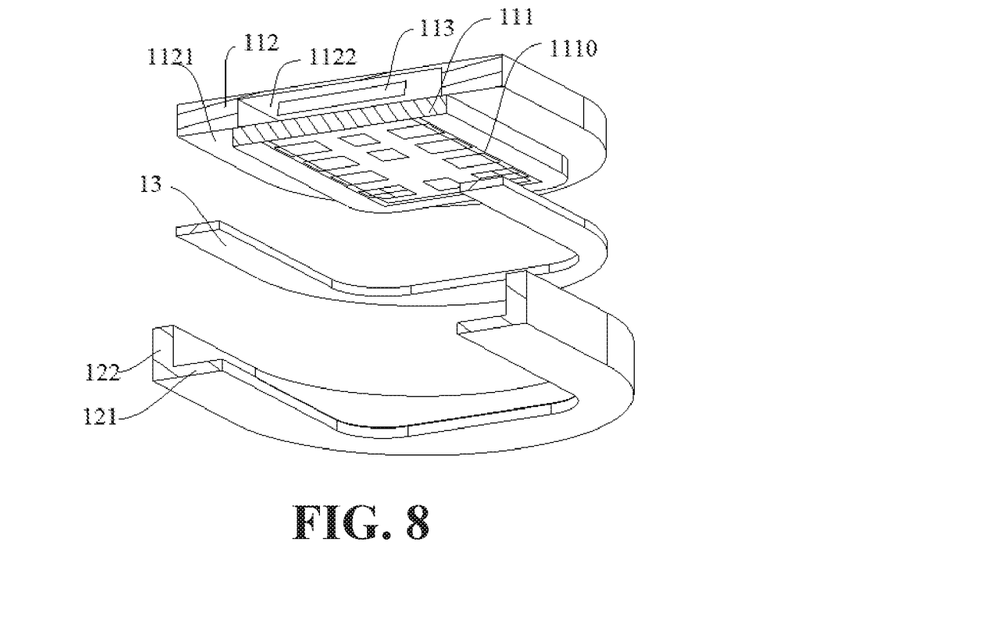
FIG. 8 is an exploded view of the fingerprint sensor of FIG. 7.

Referring further to FIG. 7 and FIG. 8, the chip assembly 11 may further include a die 113. The sealing element 112 defines a receiving cavity 1122. The die 113 is received in the receiving cavity 1122 and electrically coupled to the circuit board 111. The die 113 may be fixed to the circuit board 111 via adhesive, and the die 113 is electrically coupled to bonding pads 1110.

In some implementations, the receiving cavity 1122 may include an opening (not shown) away from the circuit board 111. That is, the sealing element 112 does not cover a surface of the die 113 away from the circuit board 111. Under this condition, the chip assembly 11 may further include a decoration layer (not indicated) covering the opening. The decoration layer may have a pattern to beautify the fingerprint sensor 200. Certainly, the fingerprint sensor 200 may also be protected by the decoration layer.

Figure 9:
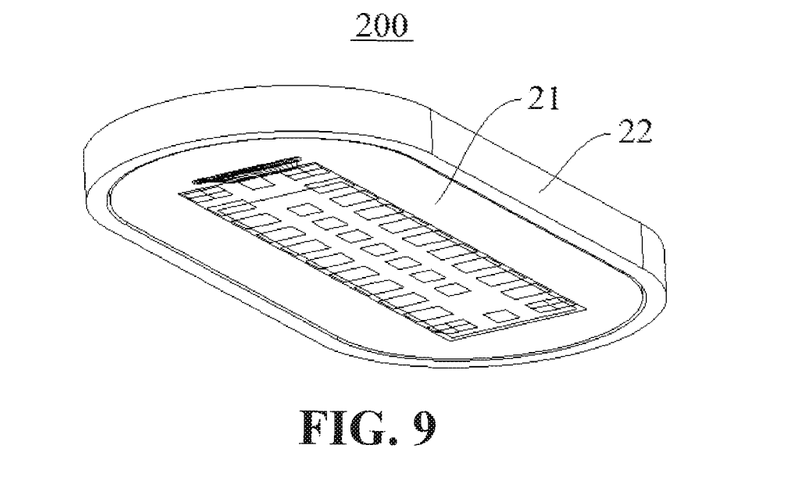
FIG. 9 is a perspective view of a fingerprint sensor in accordance with another implementation of the present disclosure.
Figure 10:
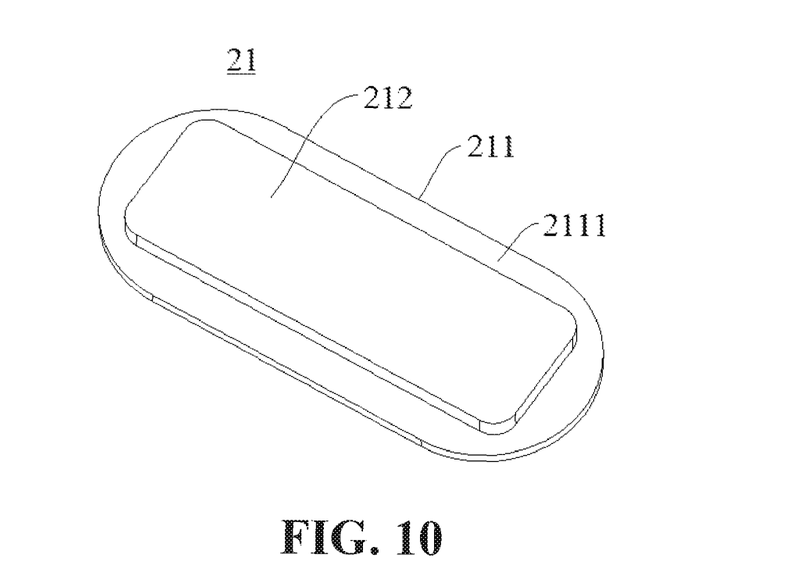
FIG. 10 is a perspective view of a chip assembly of the fingerprint sensor of FIG. 9.
Figure 11:
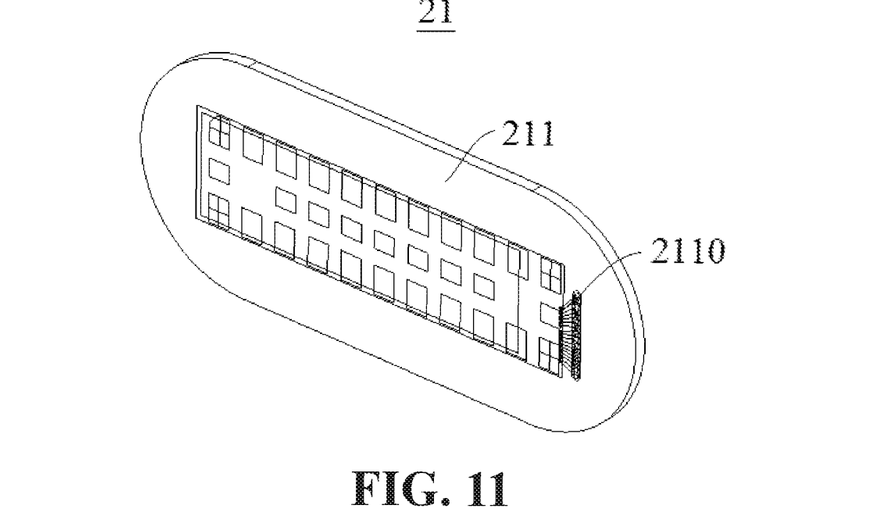
FIG. 11 is a perspective view of the chip assembly of the fingerprint sensor of FIG. 9, viewed from another viewpoint.

Referring to FIGS. 9-11, the fingerprint sensor 200 in accordance with another implementation of the present disclosure may include a chip assembly 21 and a protection assembly 22. A difference between the fingerprint sensor 100 and the fingerprint sensor 200 is that the sealing element 212 protrudes from the circuit board 211, and the circuit board 211 includes a limitation surface 2111 surrounding the sealing element 212. In the implementation, the limitation surface 2111 is annular. Certainly, in other implementations, the limitation surface 2111 may be other shapes, and the present disclosure is not limited thereto.

Figure 12:
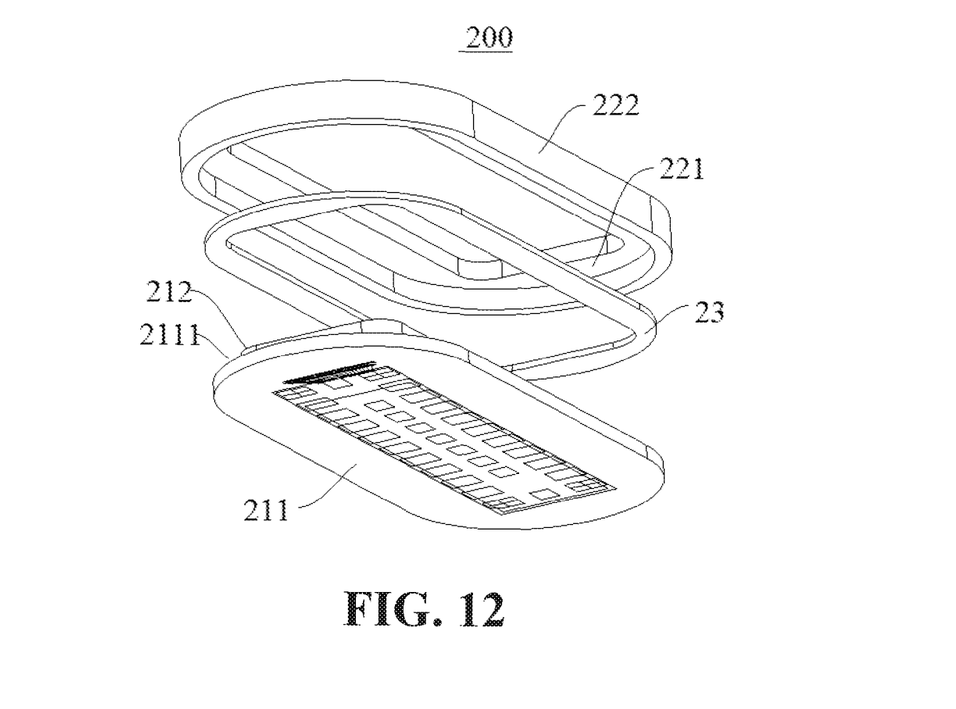
FIG. 12 is an exploded view of the fingerprint sensor of FIG. 9.
Figure 13:
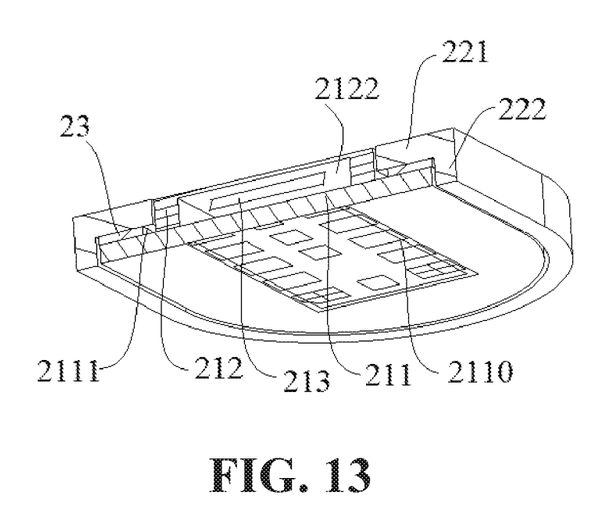
FIG. 13 is a sectional view of the fingerprint sensor of FIG. 9.
Figure 14:
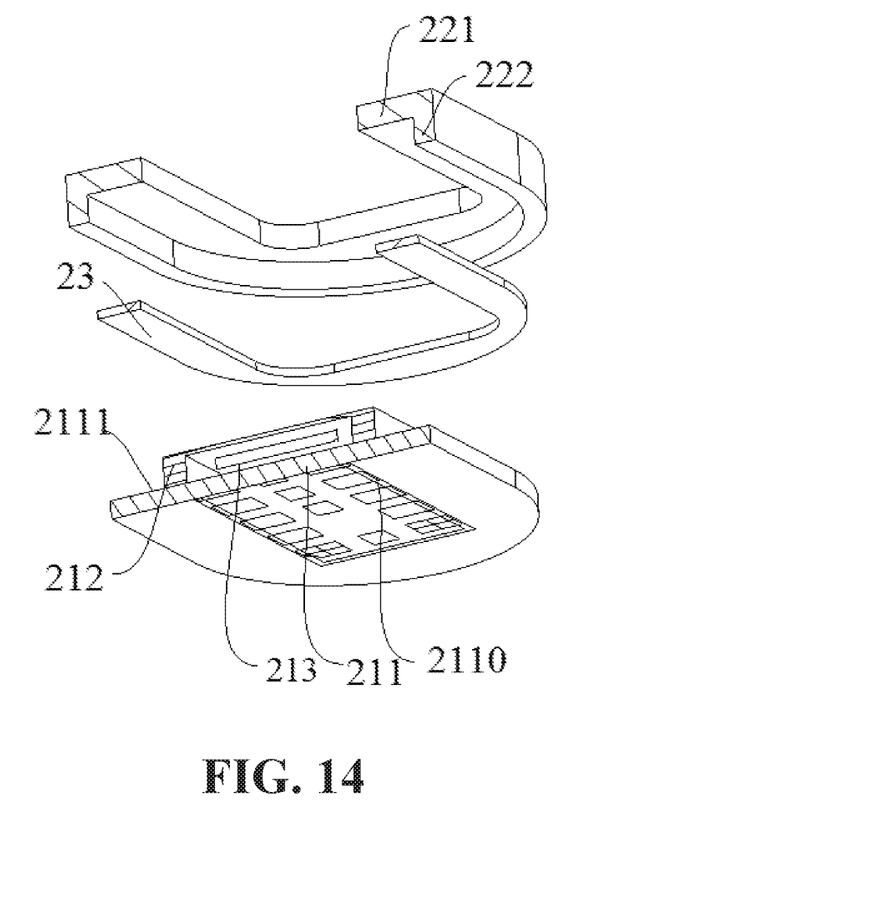
FIG. 14 is an exploded view of the fingerprint sensor of FIG. 13.

Referring further to FIGS. 12-14, the protection assembly 22 may include a first protection element 221 and a second protection element 222. The first protection element 221 is engaged with the limitation surface 2111 to surround the sealing element 212. Certainly, in other implementations, the first protection element 221 may be other shapes, what is needed is that the first protection element 221 can be engaged with the limitation surface 2111. The second protection element 222 protrudes from a side of the first protection element 221 away from the sealing element 212 and surrounds the whole peripheral side of the circuit board 211 or a portion of the peripheral side of the circuit board 211.

In the implementation, the first protection element 221 is fixed to the limitation surface 2111 via an adhesive layer 23, so that the protection assembly 22 can be fixed to the chip assembly 21. Certainly, in other implementations, the second protection element 222 may be fixed to the peripheral side of the sealing element 212, so that the protection assembly 22 can also be fixed to the chip assembly 21. Furthermore, the thickness of the first protection element 221 may be substantially the same as or less than that of the circuit board 211, or a sum of the thickness of the first protection element 221 and the thickness of the adhesive layer 23 may be substantially the same as or less than that of the circuit board 211, so that the first protection element 221 is not higher than the circuit board 211.

In the implementation, the first protection element 221 is engaged with the limitation surface 2111 of the circuit board 211 surrounding the sealing element 212. Thus, the fingerprint sensor 100 is not thick due to the protection assembly 12, so that the fingerprint sensor 100 is suitable for a thin terminal.

Furthermore, the chip assembly 21 may further include a die 213. The sealing element 212 defines a receiving cavity 2122. The die 213 is received in the receiving cavity 2122 and electrically coupled to the circuit board 211. The die 213 may be fixed to the circuit board 211 via adhesive, and the die 213 is electrically coupled to bonding pads 2110.

In some implementations, the receiving cavity 2122 may include an opening (not indicated) away from the circuit board 211. That is, the sealing element 212 does not cover a surface of the die 213 away from the circuit board 211. Under this condition, the chip assembly 21 may further include a decoration layer (not indicated) covering the opening. The decoration layer may have a pattern to beautify the fingerprint sensor 200. Certainly, the fingerprint sensor 200 may also be protected by the decoration layer.

Certainly, in other implementations, a protection assembly may be absent from a fingerprint sensor. The protection assembly may be a portion of a housing of a terminal having the fingerprint sensor, for example, the protection assembly and the housing may be integrally formed.

Figure 15:
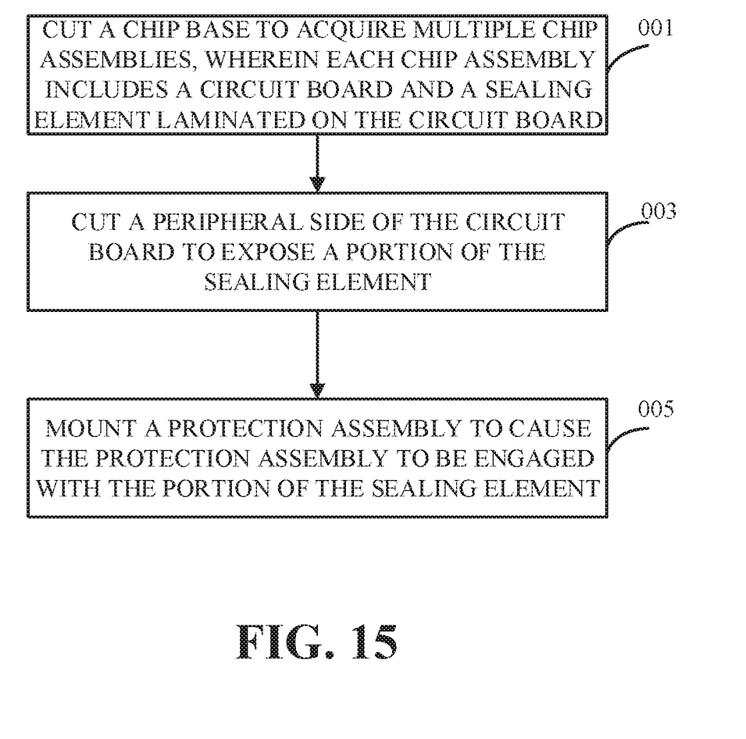
FIG. 15 is a flow chart of a method for manufacturing a fingerprint sensor in accordance with an implementation of the present disclosure.

FIG. 15 is a flow chart of a method for manufacturing a fingerprint sensor in accordance with an implementation of the present disclosure. The method may include the follows.

At block 001, a chip base is cut to acquire multiple chip assemblies. Each chip assembly may include a circuit board and a sealing element laminated on the circuit board.

At block 003, a peripheral side of the circuit board is cut off to expose a portion of the sealing element (that is, the limitation surface as described above).

At block 005, a protection assembly is mounted to cause the protection assembly to be engaged with the limitation surface of the sealing element.

In alternative implementations, at block 003, the circuit board is not cut, and a peripheral side of the sealing element is cut off to expose a portion of the circuit board (the limitation surface described above). At block 005, the protection element is engaged with the limitation surface of the circuit board.

While the present disclosure has been described in detail above with reference to the exemplary implementations, the scope of the present disclosure is not limited thereto. As will occur to those skilled in the art, the present disclosure is susceptible to various modifications and changes without departing from the spirit and principle of the present disclosure. Therefore, the scope of the present disclosure should be determined by the scope of the claims.

What is claimed is:

1. A fingerprint sensor, comprising:
   a chip assembly comprising a sealing element and a circuit board disposed on part of a surface of the sealing element; and
   a protection assembly comprising a first protection element disposed on a remaining part of the surface of the sealing element to define a space to receive the circuit board.

2. The fingerprint sensor of claim 1, wherein the protection assembly further comprises a second protection element, and the second protection element protrudes from a side of the first protection element away from the circuit board and surrounds at least a portion of a peripheral side of the sealing element.

3. The fingerprint sensor of claim 1, wherein the fingerprint sensor further comprises an adhesive layer, and the first protection element is fixed to the remaining part of the surface of the sealing element via the adhesive layer.

4. The fingerprint sensor of claim 1, wherein the first protection element is annular.

5. The fingerprint sensor of claim 1, wherein the chip assembly further comprises a die, the sealing element defines a receiving cavity, and the die is received in the receiving cavity and electrically coupled to the circuit board.

6. A fingerprint sensor, comprising:
   a chip assembly comprising a circuit board and a sealing element disposed on part of a surface of the circuit board; and
   a protection element comprising a first protection element disposed on a remaining part of the surface of the circuit board to define a space to receive the sealing element.

7. The fingerprint sensor of claim 6, wherein the protection element further comprises a second protection element, and the second protection element protrudes from a side of the first protection element away from the sealing element and surrounds at least a portion of a peripheral side of the circuit board.

8. The fingerprint sensor of claim 6, wherein the first protection element is annular.

9. The fingerprint sensor of claim 6, wherein the chip assembly further comprises a die, the sealing element defines a receiving cavity, and the die is received in the receiving cavity and electrically coupled to the circuit board.

10. A terminal, comprising:
- a housing;
- a chip assembly comprising a sealing element and a circuit board disposed on part of a surface of the sealing element; and
- a protection element connected to the housing and comprising a first protection element disposed on a remaining part of the surface of the sealing element to define a space to receive the circuit board.

11. The terminal of claim 10, wherein the protection element further comprises a second protection element, and the second protection element protrudes from a side of the first protection element away from the circuit board and surrounds at least a portion of a peripheral side of the sealing element.

12. The terminal of claim 10, wherein the terminal further comprises an adhesive layer, and the first protection element is fixed to the remaining part of the surface of the sealing element via the adhesive layer.

13. The terminal of claim 10, wherein the first protection element is annular.

14. The terminal of claim 10, wherein the chip assembly further comprises a die, the sealing element defines a receiving cavity, and the die is received in the receiving cavity and electrically coupled to the circuit board.

15. The terminal of claim 10, wherein the protection element and the housing are integrally formed.

\* \* \* \* \*